(12) United States Patent
Butts et al.

(10) Patent No.: US 10,486,157 B2
(45) Date of Patent: Nov. 26, 2019

(54) DEVICE FOR SAMPLE COLLECTION, TRANSPORTATION, AND PROCESSING

(71) Applicant: Omega Bio-tek, Inc., Norcross, GA (US)

(72) Inventors: Travis Butts, Norcross, GA (US); Qi Guo, Norcross, GA (US)

(73) Assignee: Omega Bio-Tek, Inc., Norcross, GA (US)

( * ) Notice: Subject to any disclaimer, the term of this patent is extended or adjusted under 35 U.S.C. 154(b) by 0 days.

(21) Appl. No.: 15/411,943

(22) Filed: Jan. 20, 2017

(65) Prior Publication Data

US 2017/0232437 A1 Aug. 17, 2017

Related U.S. Application Data

(60) Provisional application No. 62/278,494, filed on Jan. 14, 2016.

(51) Int. Cl.
*B01L 3/00* (2006.01)
*B01L 9/06* (2006.01)
*G01N 1/02* (2006.01)

(52) U.S. Cl.
CPC ............ *B01L 3/5029* (2013.01); *B01L 3/545* (2013.01); *B01L 9/06* (2013.01); *B01L 2200/18* (2013.01); *B01L 2300/021* (2013.01); *B01L 2300/0829* (2013.01); *G01N 2001/028* (2013.01)

(58) Field of Classification Search
CPC .......... B01L 3/5029; B01L 9/06; B01L 3/545; B01L 2200/18; B01L 2300/021; B01L 2300/0829; B01L 3/50853; B01L 9/523; C12N 15/1003; G01N 2001/028; G01N 1/10
See application file for complete search history.

(56) References Cited

U.S. PATENT DOCUMENTS

2003/0157728 A1* 8/2003 Uhl .................... A61B 10/0051
436/177
2007/0299364 A1* 12/2007 Sangha .................. A61F 13/38
600/572
2013/0288343 A1* 10/2013 Page .................. A61B 10/0051
435/283.1

* cited by examiner

*Primary Examiner* — Sally A Merkling
(74) *Attorney, Agent, or Firm* — Thomas | Horstemeyer, LLP (57) ABSTRACT

A device system, and method of use thereof, for collecting, transporting, and processing a biological sample is provided.

14 Claims, 6 Drawing Sheets

DEVICE FOR SAMPLE COLLECTION, TRANSPORTATION, AND PROCESSING

CROSS-REFERENCE TO RELATED APPLICATIONS

This application claims priority benefit from U.S. Provisional Application Ser. No. 62/278,494, filed on Jan. 14, 2016, which is incorporated herein by reference in its entirely.

FIELD OF THE INVENTION

The present invention relates generally to sample collection, transportation, and processing.

BACKGROUND OF THE INVENTION

Swabs provide an economical and non-invasive method for collection and transportation of biological samples from buccal, fecal, sweat, semen, whole blood samples and other bodily fluids. The swab samples can be collected at multiple sites then have to be transported to a processing location for molecular biological applications. Receiving locations running a large amount of samples for analysis can implement liquid handlers and magnetic processors to help aid in the processing of the samples. These instruments require that the samples be in 24, 96 or 384 well formats with 96-well formats being the most common. The receiving locations must take the received swab samples from the individual packaging then place them into a 96-well plate and correctly catalog the correct location of the swab well. The process of placing the samples in a 96-well format is manual and leads to possible sample switching in either placing the sample in the wrong well or documentation of the sample location within the well.

Swabs must be lysed to analyze the DNA, RNA or proteins from the cells contained on the swab. This generally requires the swabs to be placed in a lysis buffer that may require heating, mechanical, or enzymatic treatments. After lysis, the swabs must be removed from the liquid to obtain the desired DNA, RNA or proteins. Alternatives to swabs on the market such as whole blood can be invasive in their collection method while saliva collection devices exist on the market such as DNA Genotek Oragene collection devices but these require the donor to provide a large amount of saliva which can be difficult for children or animals. These existing collection devices then transfer the biological material to a stabilization solution which may be incompatible with the processing laboratories chemistry for DNA, RNA or protein extraction. The Promega SlicPrep 96 device allows the customer to raise and lower the swabs into a lysis buffer but cannot identify the location in which the swabs have been inserted and requires the laboratory to manually identify the locations.

SUMMARY OF THE INVENTION

The invention provides a device system, and method of use thereof, for collection, transportation, identification and processing biological samples. In certain embodiments, the invention device system is used for collecting biological samples using buccal swabs and/or any other tools suitable for collecting biological samples, now known or later developed in the art. The invention further provides a method to allow for sample collection, transportation, and processing by the laboratory without the need to manually transfer the biological sample into another sample collection tube which will then be placed in a well position of a 96-well microtiter plate.

In certain embodiments, the invention provides a device system for collecting, transporting, and processing a biological sample, comprising: a) a detachable sample collection assembly; b) collection and/or extraction basket; c) place holder; and d) hinged holder. In certain embodiments, the invention provides that a detachable portion of the invention device can be attached to corresponding paperwork, and the position in which it is inserted into the 96-well microtiter plate can be read by a barcode reader and/or any other readers, now known or later developed in the art for identification or label purposes. In certain embodiments, the invention provides how the swabs biological material can be transferred into the liquid and then further processed with liquid handling instruments or magnetic processors.

The biological samples as used herein refer to any bodily fluid, tissue, organ, and/or cells including, but not limited to, buccal mucosa or cheek tissue, whole blood, plasma, urine, feces, skin, hair, and organ tissue.

The invention also provides that the invention device system is used for processing the biological samples for nucleic acid (e.g., DNA and/or RNA) and/or protein extractions, and/or any laboratory analytic analysis.

Other features and advantages of the invention become apparent to those skilled in the art upon review of the following detailed description, claims and drawings in which like numerals are used to designate like features.

BRIEF DESCRIPTION OF THE DRAWINGS

This patent application file contains at least one drawing executed in color. Copies of this patent application with color drawing(s) will be provided by the Office upon request and payment of the necessary fee.

FIG. 1. The sample collection piece. The device has a swab portion which can be cotton, polyester, and other material used to collect the donor sample by brushing against the donor. The swab portion is attached to a thin wooden or plastic cylindrical shaft which attaches to a circular disc. The disc is a cap to the collection/extraction basket and can attach via screwing into the basket or snapping in. On the other side of the shaft in the middle of the disc, a 2-D barcode is printed or a sticker is placed on the disc. A different thin cylindrical shaft is attached to the disc from the opposite side of the other cylindrical shaft protruding from the same side as the 2-D barcode. The second shaft is offset to the side of the disc. The second cylindrical shaft attaches to a flat rectangular portion which a barcode may be attached via sticker or printing.

Before the embodiments of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein are for the purpose of description and should not be regarded as limiting.

DETAILED DESCRIPTION OF THE INVENTION

The invention provides a device system for collecting, transporting, and processing a biological sample, comprising: a) a sample collection assembly; b) a collection extraction basket; c) a place holder; and d) a hinged holder.

In certain embodiments, the sample collection assembly comprises a) a swab, b) a cap, and c) a handle comprising an area for a barcode or sample identification. In certain embodiments, the swab, the cap, and the handle, each can be detachable from each other.

Figure 1:
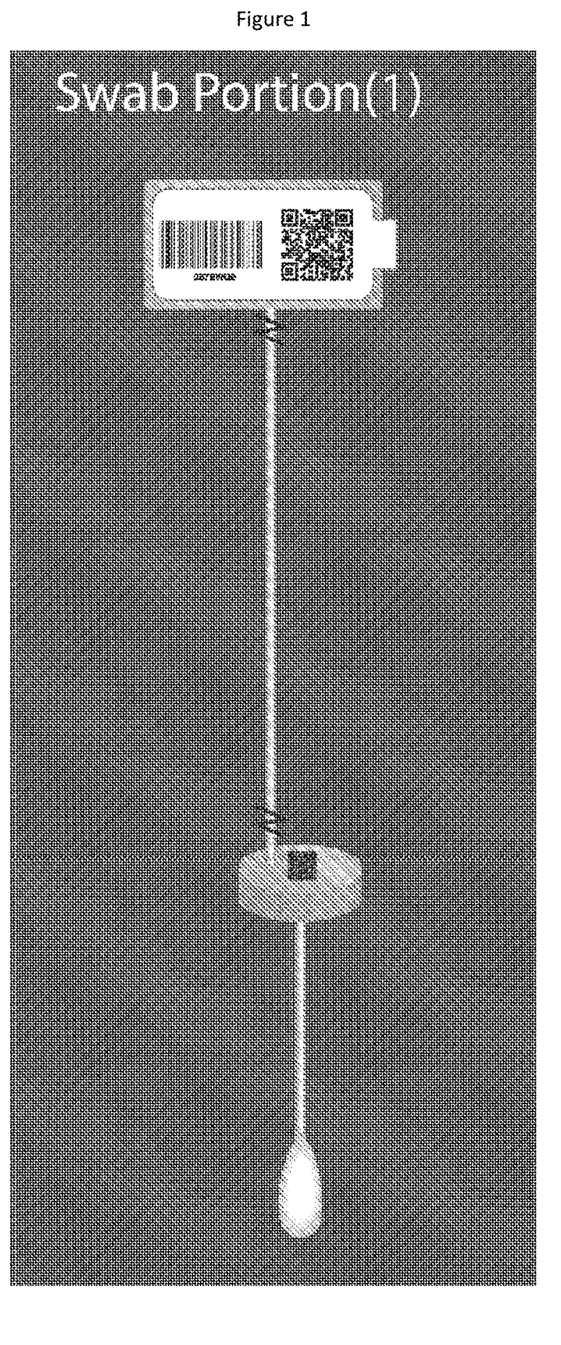

As illustrated in FIG. 1, the swab (1) with or without removing the handle can be inserted into the collection extraction basket (2) and the cap provides a lid for the collection and/or extraction basket (2). In certain embodiments, the cap or lid contains a sticker or imprinted sample identification via barcode which matches the removable sample identifier. In certain embodiments, the handle contains a removable sample identifier, including but not limited to, sticker or printing, which can be removed by either removal of the sticker or breaking off.

In certain embodiments, the swab is a buccal swab which can be used for collection of any cheek tissue samples, whole blood, feces, urine, skin, hair, including forensic samples.

Figure 2:
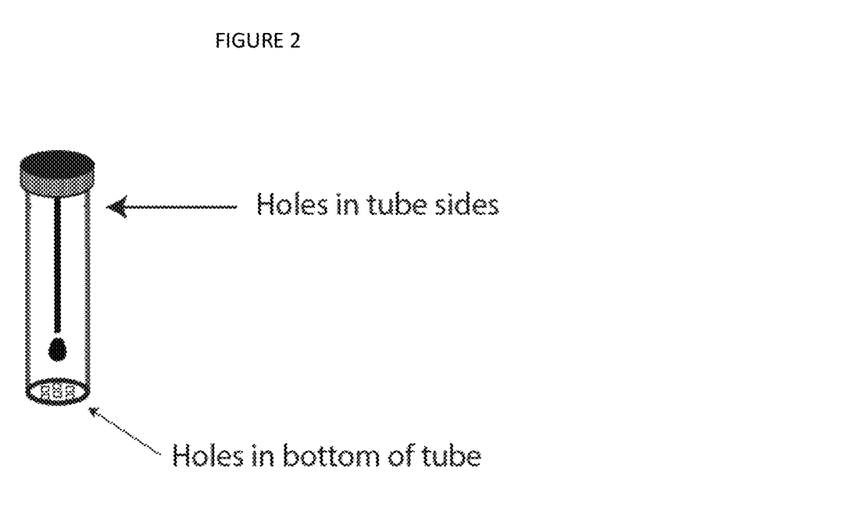
FIG. 2: The basket/collection piece. The piece has a flat circular disc bottom which includes a 2×2 grid pattern. The holes are on the outside segments of the grid pattern and are not bigger than 1×1 mm. Cylinder walls attach to the disc to create the basket shape with an opening at the top. On the cylinder walls a barcode may be printed. The cylinder walls also include a small opening to allow air flow. The basket collection piece has an outer plastic lip around the top of the device.

In certain embodiments, the collection extraction basket also comprises a barcode and/or any other readable identifier which matches the sample identifier labeled on either the cap or the handle of the detachable sample collection assembly. In certain embodiments, the collection extraction basket comprising tubes having small holes at the bottom that allow for liquid to enter the collection and/or extraction basket without removing the swab.

In certain embodiments, the collection extraction basket (2) with the detachable sample collection assembly (1) can be placed for centrifugation where the biological sample on the swab is in contact with a sample processing solution. After the centrifugation, the biological sample remains in the sample processing solution while the swab can be discharged. In certain embodiments, the remaining sample processing solution comprising the biological sample can be removed from the collection extraction basket during the centrifugation if the collection extraction basket is above liquid level.

In certain embodiments, the collection extraction basket (2) with the detachable sample collection assembly (1) is used as a transport chamber for transporting and/or shipping samples collected without additional transferring steps.

Figure 3:
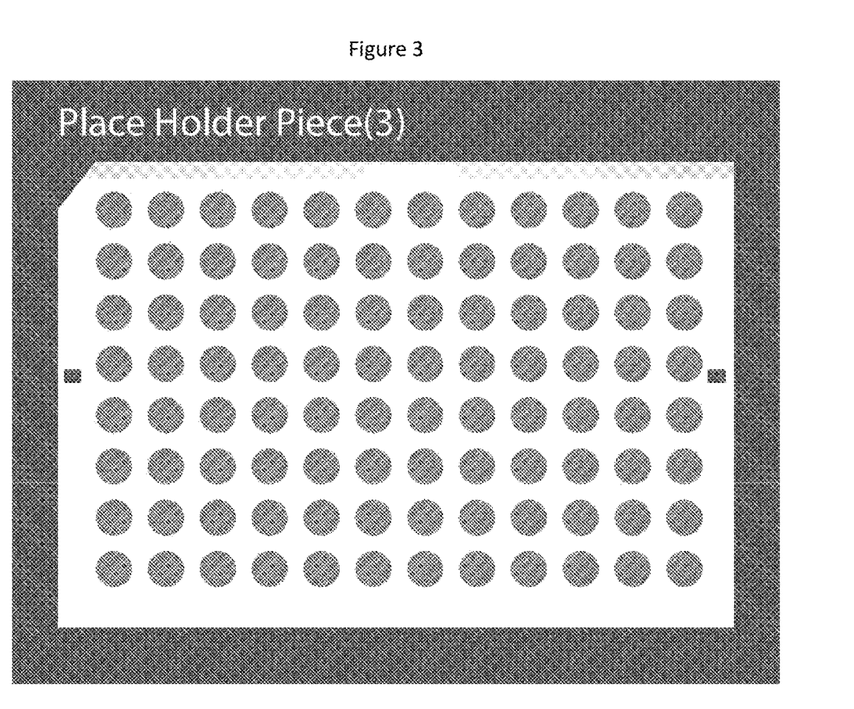
FIG. 3. The place holder piece (top view). A flat rectangular piece with holes that are slightly larger than the basket collection piece, arranged in a 12×8 pattern. Two square holes are on the outer edges of the piece on the short side. The square holes are slightly larger than the notches present on the hinged holder piece. On the short sides of the rectangular holder piece, flat pieces extend slightly vertically and are not higher than 3 mm or longer than 5 mm.
Figure 4:
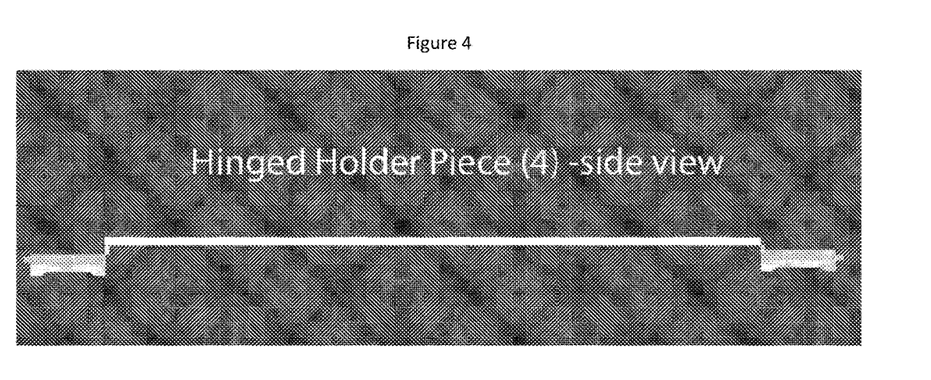
FIG. 4. Hinged Holder Piece (side view). A flat rectangular piece with holes, that are slightly larger than the basket collection piece, arranged in a 12×8 pattern. Two hinged pieces extend off the short side of the rectangular hinged holder piece which are the same width dimensions as the rectangular hinged holder piece. On the end of the hinged piece is a rectangular piece protruding that is approximately 0.5×0.5×0.5 mm. This protruding piece when the hinged pieces are placed vertically aligns with the place holder piece's two square holes and can be inserted into them.
Figure 5:
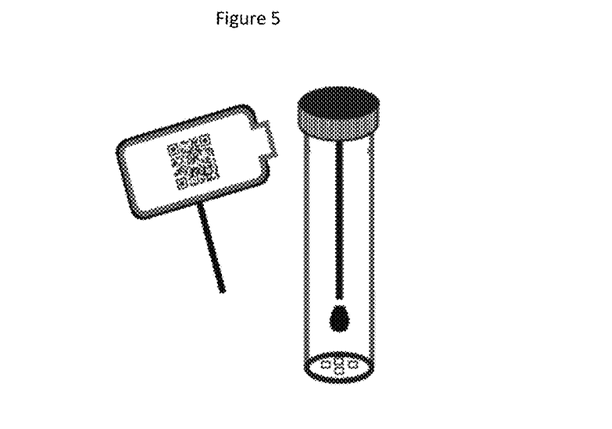
FIG. 5. Assembled collection/extraction basket and swab portion. The top cylinder shaft has been removed and a sample collection piece inserted into the basket/collection piece.
Figure 6:
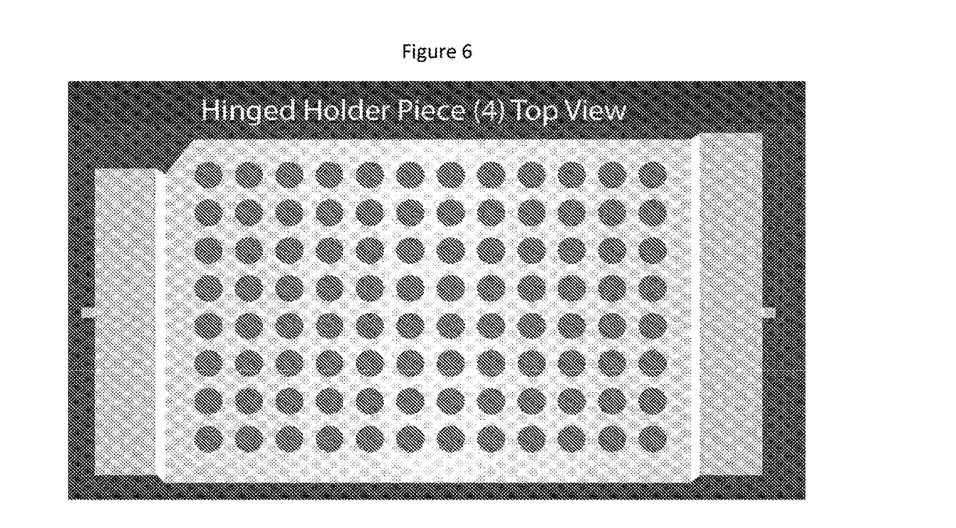
FIG. 6. Top view of the place holder piece.
Figure 7:
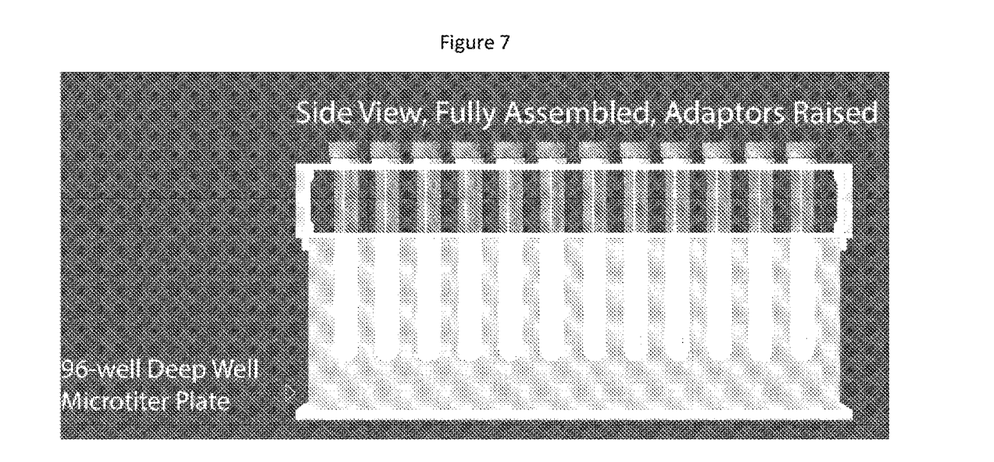
FIG. 7. Side View, Fully Assembled, Adaptors Raised without liquid. The place holder piece and hinged holder piece are laying on top of a 96-well deep, well plate in the raised position. Ninety-six (96) basket/collection pieces have been inserted into the pieces.
Figure 8:
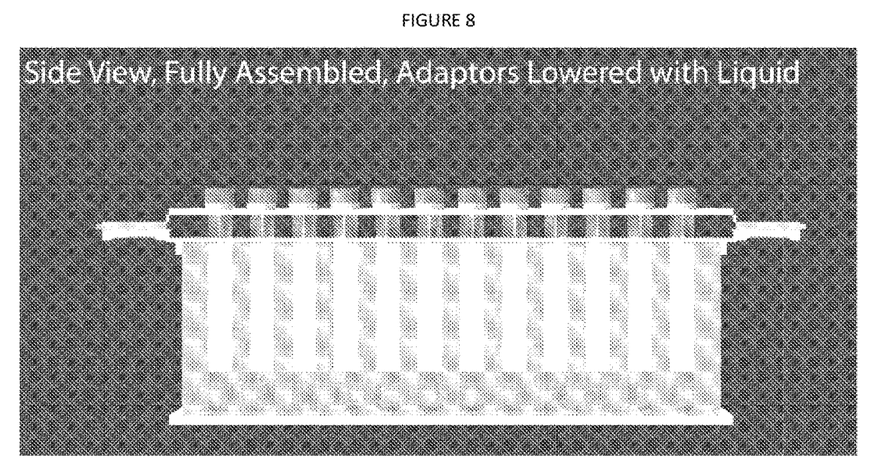
FIG. 8. Side View, Fully Assembled, Adaptors lowered with liquid. The place holder piece and hinged holder piece are laying on top of a 96-well deep, well plate in the raised position. 96 basket/collection pieces have been inserted into the pieces.
Figure 9:
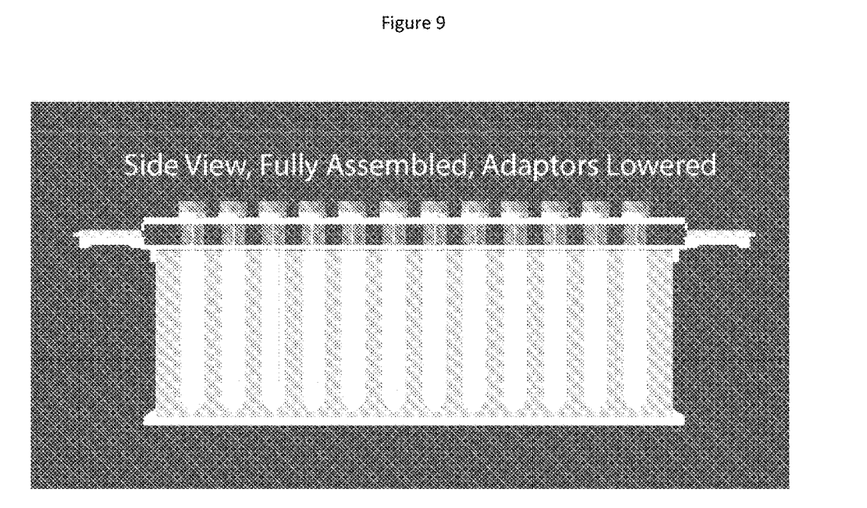
FIG. 9. Side View, Fully Assembled, Adaptors lowered without liquid. The place holder piece and hinged holder piece are laying on top of a 96-well deep, well plate in the lowered position. Ninety-six (96) basket/collection pieces have been inserted into the pieces.
Figure 10:
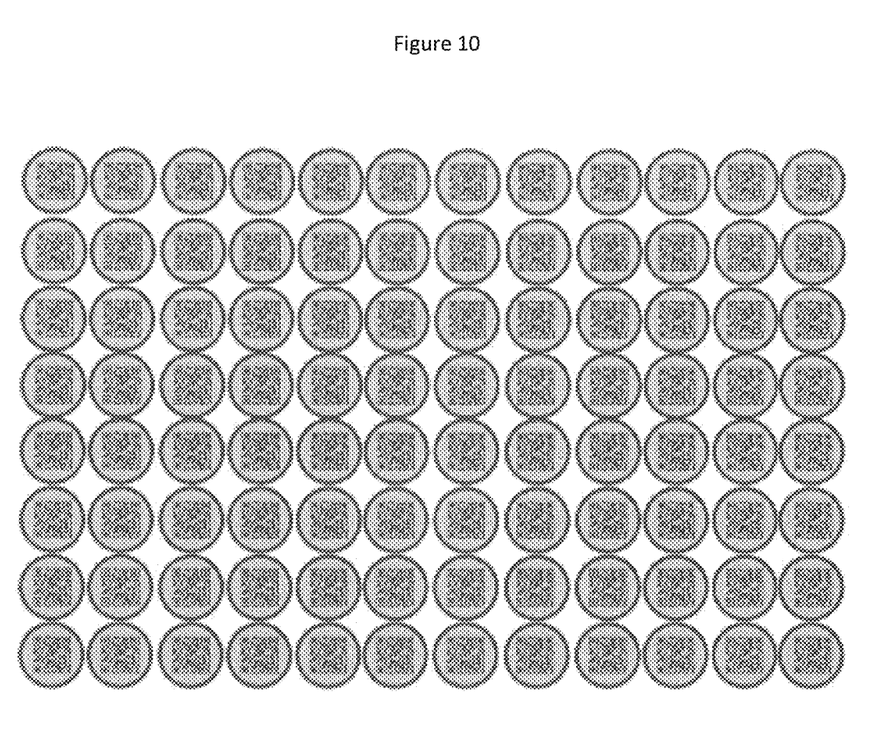
FIG. 10. Top View of Assembled collection/extraction basket and swab portion. The top cylinder shaft has been removed and sample collection piece inserted into the basket/collection piece. Barcode on the top of cylinder could be scanned.

In certain embodiments, the place holder (3) of the invention device system is for alignment and support between the detachable sample collection assembly (1) and the collection extraction basket (2). In certain embodiments, the place holder is made of polypropylene or other suitable polymers, glass, and/or plastic materials. In certain embodiments, the place holder is a plastic cover comprising 96 wells corresponding and/or suitable to be laid on top of a 96-deep well microtiter plate. The invention encompasses other type of plastic and/or polymer holders comprising different numbers of wells (e.g., 24 wells, 48 wells, etc.) which correspond to and/or are suitable to be laid on top of a microtiter plate with the same number of wells.

In certain embodiments, the invention device system further comprises a hinged holder (4) also comprising 96 spaces corresponding to a 96-well microtiter plate. The hinged holder allows for the detachable sample collection assembly (1) and the collection extraction basket (2) to be inserted into the spaces but limit the top of the detachable sample collection assembly (1) and the collection extraction basket (2) from fully passing through the hinged holder piece (4). Once the detachable sample collection assembly (1) and the collection extraction basket (2) are inserted into the place holder (3) and the hinged holder (4), the barcodes on each individual sample can be read with a 2-D barcode reader thus identifying the position of the well containing each sample.

In certain embodiments, the hinged holder (4) has two positions. When hinges are horizontal to the microtiter plate, it is in the lowered position which lowers the detachable sample collection assembly (1) and the collection extraction basket (2) containing the biological material to be in contact and/or merged with the sample processing solution pre-placed in each well of the 96-deep well microtiter plate. When hinges are extended vertically and lock into the place holder (3), it is in a raised position where the detachable sample collection assembly (1) and the collection extraction basket (2) are at the level above the sample processing solution. The device in this raised position can then be placed into a centrifuge to separate and remove the component containing the nucleic acids (e.g., DNA and/or RNA) or protein from the swab, and for further sample processing, such as DNA, RNA, or protein extraction, isolation, purification, and analysis.

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the amended claims along with the full scope of equivalents to which those claims are entitled.

EXAMPLES

Using this device, the medical staff or donor will swab the donor then place the swab portion of the device in the collection basket. The identification portion from the swab is placed on the paperwork accompanying the donor's sample. The swab/basket and paperwork is then shipped to the molecular biology laboratory for testing. When received, the laboratory can fill a 96-deep well plate with lysis buffer and then place the swab/basket into a detachable collection assembly without the need for identifying the well which the sample is placed into. Once fully assembled, a barcode scanner/reader can take an image of the assembled detachable collection device thus identifying the location of each sample and the corresponding well location. The detachable assembly can then be lowered into the lysis buffer to release the DNA from the cells contained on the swab. The detachable assembly can then be raised above the liquid level and then centrifuged to remove any remaining liquid absorbed by the swab. The detachable assembly can then be discarded which contains the swab sample. The DNA, RNA or protein has been transferred to the lysis buffer in the 96-well deep, well plate where it can be further processed by liquid handlers or magnetic processors.

The present invention is not to be limited in scope by the specific embodiments described herein. Indeed, various modifications of the invention in addition to those described herein will become apparent to those skilled in the art from the foregoing description. Such modifications are intended to fall within the scope of the amended claims.

All patents, applications, publications, test methods, literature, and other materials cited herein are hereby incorporated by reference in their entirety as if physically present in this specification.

Various features of the invention are set forth in the following claims.

What is claimed is:

1. A device system for collecting, transporting, and processing a biological sample in each well of a microtiter plate, the device system comprising:
   a) a collection unit, comprising:
      a sample collection assembly comprising a swab, a cap comprising a first sample identifier, and a flag with a handle or a pole, wherein the flag comprises a second sample identifier; and
      a collection extraction basket comprising a tubular wall, a bottom having holes, a top, and a lip, wherein the collection extraction basket is configured to receive the sample collection assembly, and wherein the swab is inserted inside of the collection extraction basket and the cap snaps or screws into the top of the collection extraction basket, and wherein the collection extraction basket comprising a third sample identifier, wherein the first, second, and third sample identifiers all match to identity the biological sample on the swab;
   b) a sample holder system, comprising:
      a microtiter plate having a top surface and a plurality of wells;
      a place holder comprising a cover with a plurality of holes positioned corresponding to the plurality of wells in the microtiter plate and corner casings to allow the place holder to fit secured on the top surface of the microtiter plate; and
      a hinged holder comprising a plate with a plurality of holes and a protruding hinge on each side of the hinged holder, wherein the plate of the hinged holder positioned corresponding to the cover of the place holder, and the hinged holder configured to attach to the place holder in two positions:
         a lowered position, where a bottom surface of the hinged holder contacts a top surface of the place holder, or
         a raised position, where the hinged holder snaps into the place holder via the protruding hinges with the bottom surface of the hinged holder being substantially parallel to the top surface of the place holder without being in contact;
   wherein the sample holder system is configured to receive a plurality of collection units, and wherein one collection extraction basket corresponds with one well of the microtiter plate, each collection extraction basket received through the hinged holder into the place holder and the microtiter plate, where the lip of each collection extraction basket when inserted to the hinged holder prevents the top of each collection extraction basket from passing through a hole of the hinged holder.

2. The device system of claim 1, wherein the swab, the cap, and the flag with the handle are detachable from each other.

3. The device system of claim 1, wherein said first, second, and third sample identifier is a barcode.

4. The device system of claim 1, wherein said collection extraction basket further comprises small holes in the tubular wall configured to allow solution to enter the collection extraction basket.

5. The device system of claim 1, wherein said place holder is made of polypropylene or other suitable polymers, glass, or plastic materials.

6. The device system of claim 5, wherein said place holder is made of a plastic and comprises holes corresponding to each well of the microtiter plate.

7. The device system of claim 1, wherein said hinged holder comprises holes corresponding to each well of the 96-well microtiter plate.

8. The device system of claim 1, wherein said biological sample comprises tissue, blood, urine, feces, skin, hair, or any other bodily fluid or mucosa.

9. A method of extracting nucleic acid or protein, comprising the step of:

a) collecting and transporting a biological sample using the device system of claim 1, and
b) processing the biological sample for the nucleic acid or protein extraction, isolation, or purifications.

10. The device system of claim 1, wherein the bottom of the collection extraction basket comprises a grid pattern in a disc and the holes are located on outside segments of the grid pattern.

11. The device system of claim 10, wherein the holes are about 1 mm×1 mm or less.

12. The device system of claim 1, wherein the hinged holder further comprises a tab projecting from each protruding hinge and the place holder comprises slots in the top surface configured to receive each tab to place the hinged holder in the raised position.

13. The device system of claim 12, wherein the tab projecting from each protruding hinge is about 0.5 mm×0.5 mm×0.5 mm.

14. The device system of claim 1, wherein the microtiter plate is a 96-well microtiter plate.

* * * * *